US00PP13386P2

(12) United States Plant Patent
Mowrey et al.

(10) Patent No.: US PP13,386 P2
(45) Date of Patent: Dec. 17, 2002

(54) STRAWBERRY PLANT NAMED 'SONORA'

(75) Inventors: Bruce D. Mowrey, Watsonville, CA (US); Larry T. Kodama, Freedmon, CA (US); JoAnne F. Coss, Salinas, CA (US); Joseph I. Espejo, Jr., Watsonville, CA (US); Thomas M. Sjulin, Aromas, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 3 days.

(21) Appl. No.: 09/703,521

(22) Filed: Nov. 1, 2000

(51) Int. Cl.[7] ..... A01H 5/00
(52) U.S. Cl. ..... Plt./209
(58) Field of Search ..... Plt./209

*Primary Examiner*—Bruce R. Campell
*Assistant Examiner*—Anne Marie Grünberg

(74) *Attorney, Agent, or Firm*—Pennie & Edmonds, LLP

(57) ABSTRACT

This invention relates to a new and distinct variety of strawberry named 'Sonora'. The present variety is similar to the varieties 'Commander', 'San Juan' and 'Ana Maria'. The present variety is fully everbearing, and is further distinguished from 'Commander', 'San Juan' and 'Ana Maria', in particular, by its flat globose habit, strong interveinal blistering, weak leaf glossiness, rounded terminal leaflet shape of base and teeth, sparse petiole pubescence, dense to very dense stolon pubescence, a position of inflorescence above the foliage, larger calyx diameter relative to the corolla, a semi-erect attitude of the fruiting truss at first picking, predominantly conical fruit, very slight to slight differences between shapes of primary and secondary fruits, very narrow to narrow band without achenes, very weak unevenness of surface of the fruit, weak to medium glossiness of the fruit, spreading to reflexed pose of the calyx segments, even flesh color of the fruit, and absent to small hollow center size.

5 Drawing Sheets

BACKGROUND OF THE INVENTION

The new variety, 'Sonora', originated as a result of a controlled cross between the strawberry plants '33×257' and 'L2' (both unpatented varieties of Driscoll Strawberry Associates, Inc.) in an ongoing breeding program, and was discovered as a seedling in a controlled breeding plot in Monterey County, Calif. The original seedling of the new cultivar was asexually propagated by stolons at a Nursury in McArthur, Shasta County, Calif. Propagules were transplanted to a controlled breeding plot in Monterey County, Calif., where the variety was identified and selected for further evaluation in May 1996. The new variety, 'Sonora', was subsequently asexually propagated and underwent further testing in the Monterey Bay area in California for five years. This propagation and testing has demonstrated that the combination of traits disclosed herein which characterize the new variety are fixed and are retained true to type through successive generations of asexual reproduction.

SUMMARY OF THE INVENTION

The present invention relates to a new and distinct variety of strawberry named 'Sonora'. The varierty is botanically identified as *Fragaria×ananassa*. The new variety is distinguished from other varieties by a number of characteristics as set forth in Tables 1–4.

COMPARISON TO SIMILAR VARIETIES

The varieties that we believe to be similar to 'Sonora' from those known to us are 'Commander' (U.S. Plant Pat. No. 7,024), 'San Juan' (U.S. plant application Ser. No. 09/524,581), and 'Ana Maria' (U.S. Plant Pat. No. 11,035). There are several characteristics of the new variety that are different from, or not possessed by, 'Commander', 'San Juan' and 'Ana Maria'. The new variety is fully everbearing and has a flat globose habit, strong interveinal blistering, weak leaf glossiness, rounded terminal leaflet shape of base and teeth, sparse petiole pubescence, dense to very dense stolon pubescence, a position of inflorescence above the foliage, larger calyx diameter relative to the corolla, a semi-erect attitude of the fruiting truss at first picking, predominantly conical fruit, very slight to slight differences between shapes of primary and secondary fruits, very narrow to narrow band without achenes, very weak unevenness of surface of the fruit, weak to medium glossiness of the fruit, spreading to reflexed pose of the calyx segments, even flesh color of the fruit, and absent to small hollow center size.

BRIEF DESCRIPTION OF THE DRAWINGS

The accompanying photographs show typical specimens of the new variety, including fruit, foliage and flowers, in color as nearly true as reasonably possible in illustrations of this type.

DESCRIPTION OF THE NEW VARIETY

Figure 1:
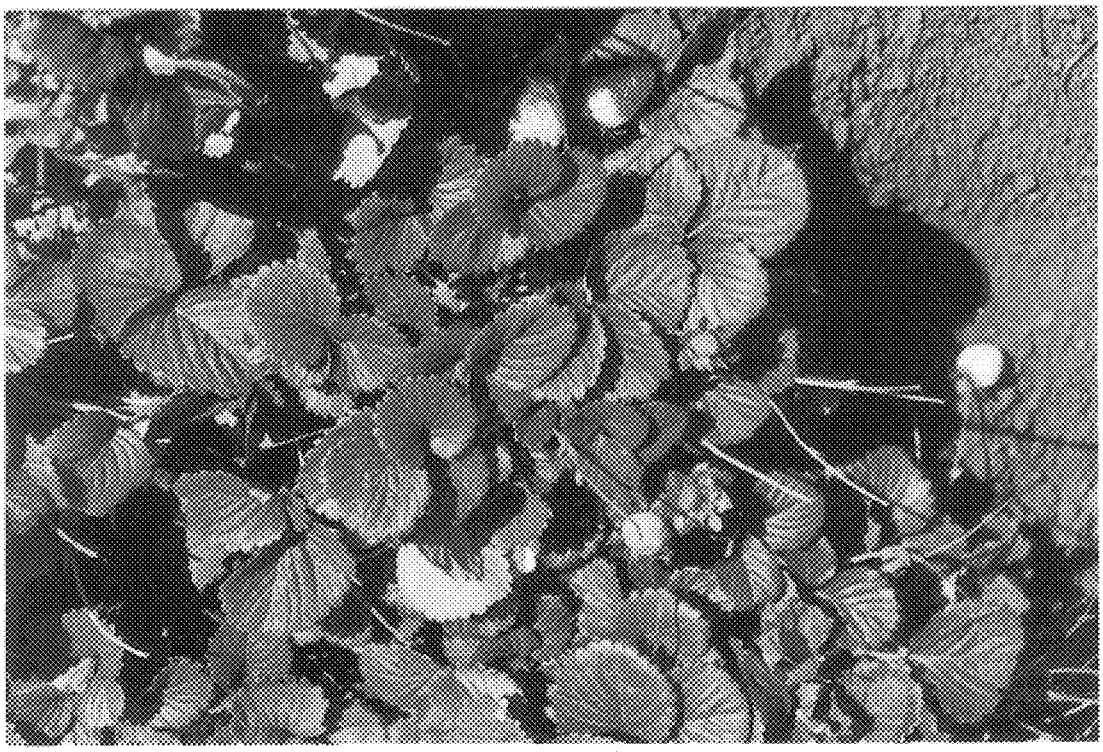
FIG. 1 shows the whole plant.
Figure 2:
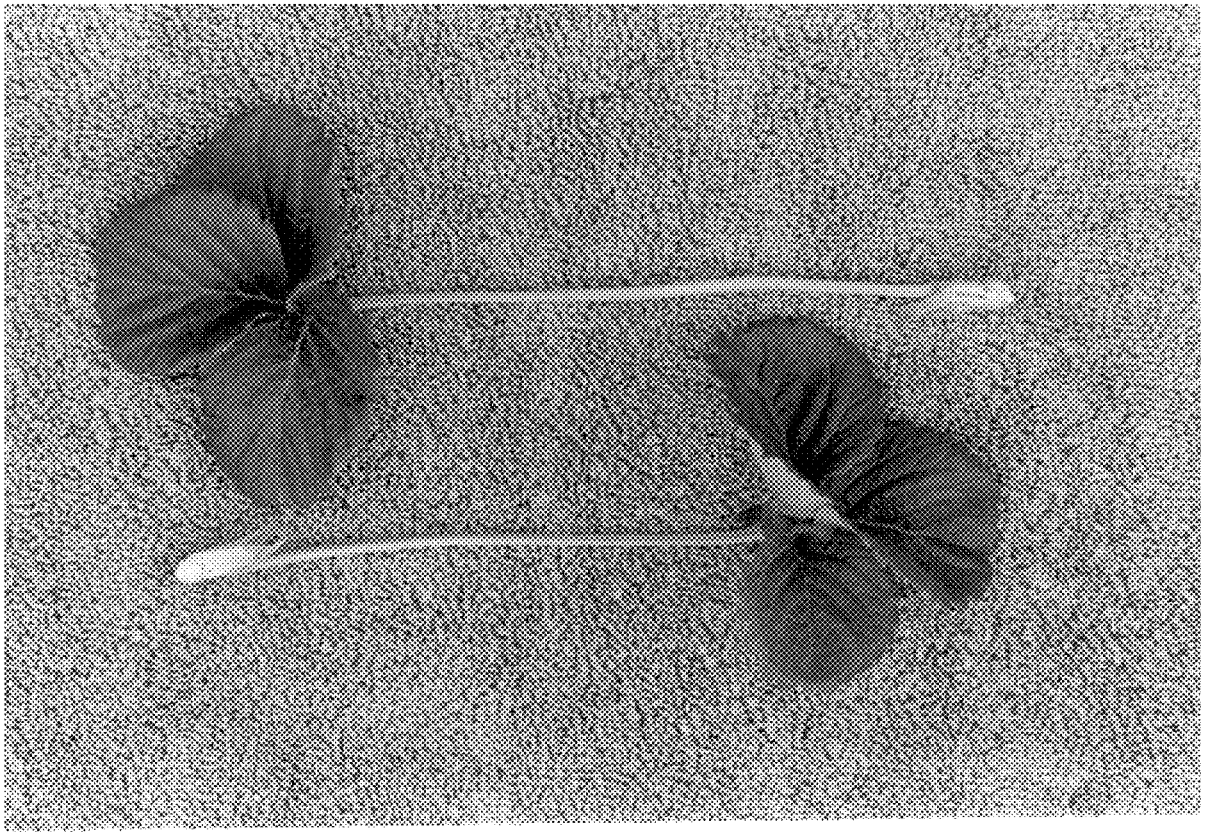
FIG. 2 shows the leaves of the plant.
Figure 3:
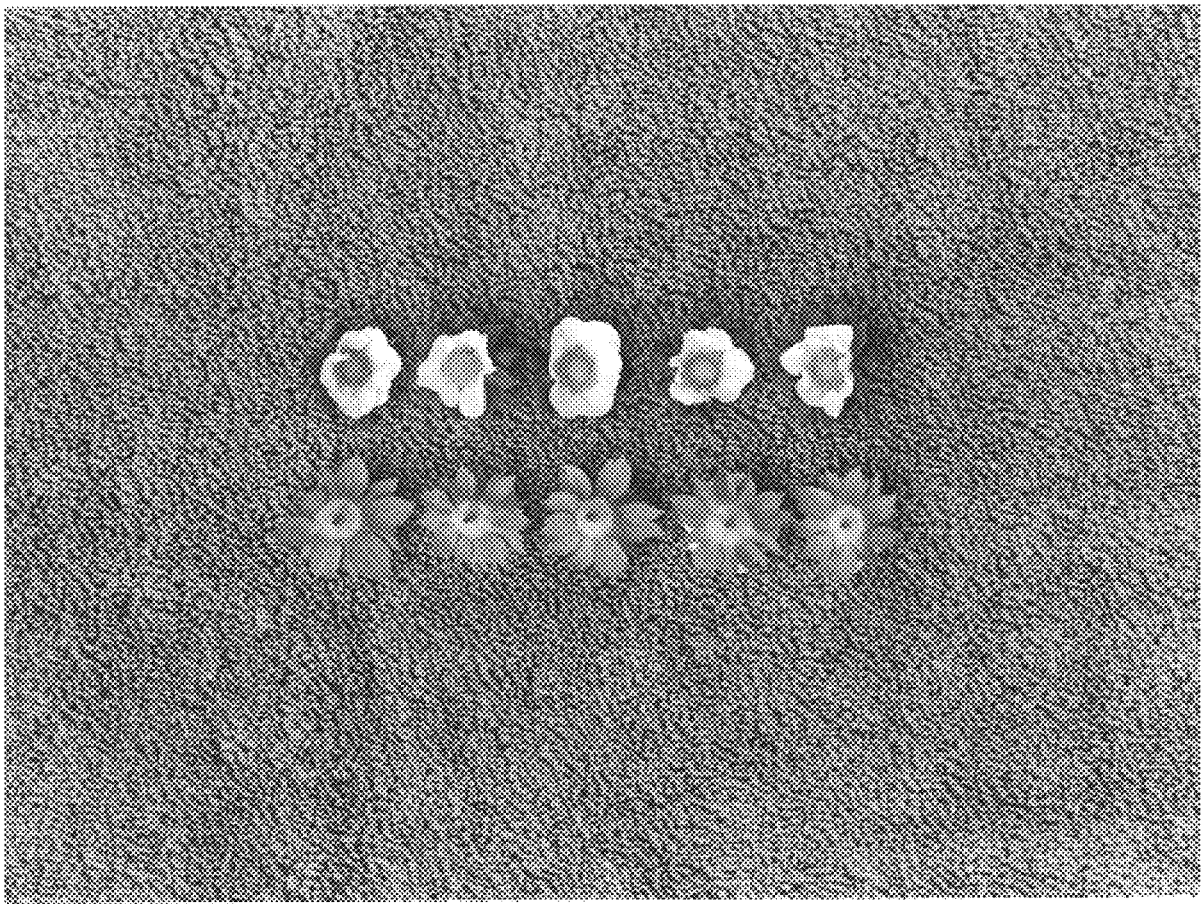
FIG. 3 shows the upperside and the underside of the flowers.
Figure 4:
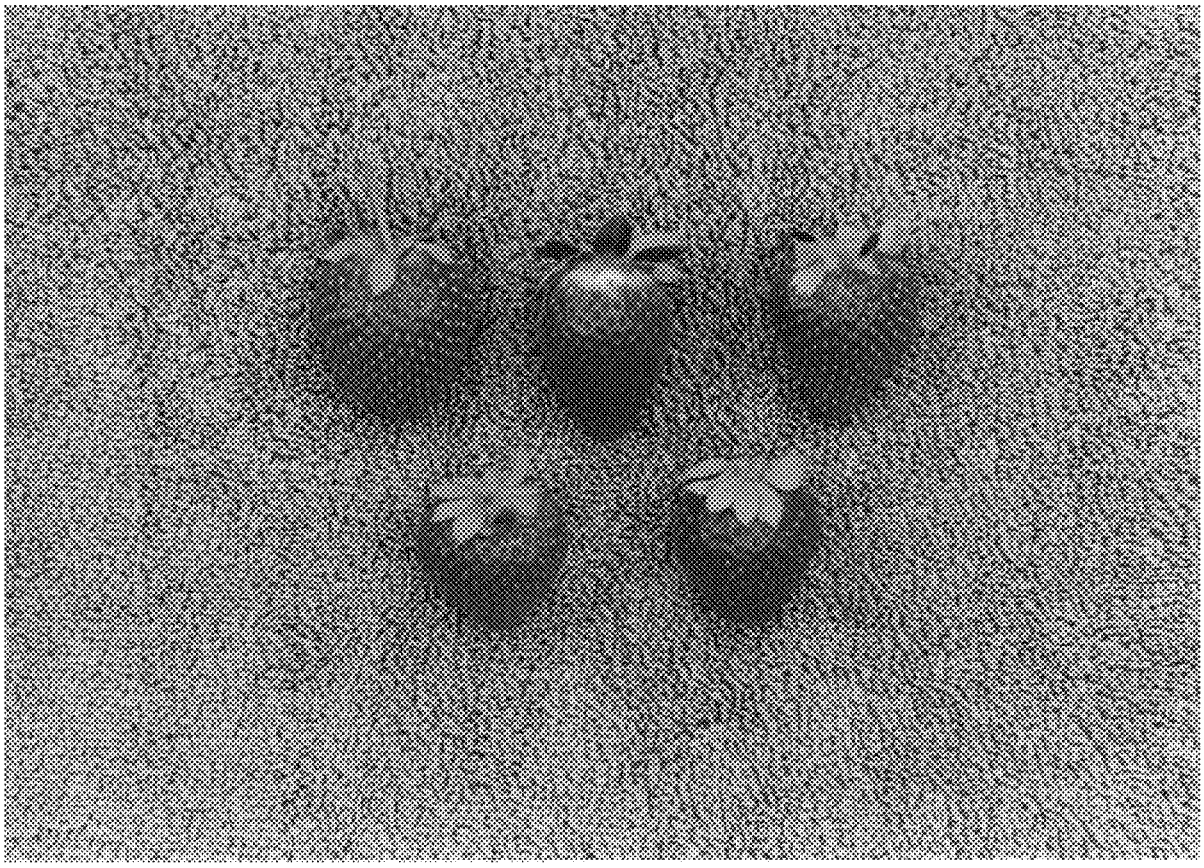
FIG. 4 shows a close-up view of the fruit.
Figure 5:
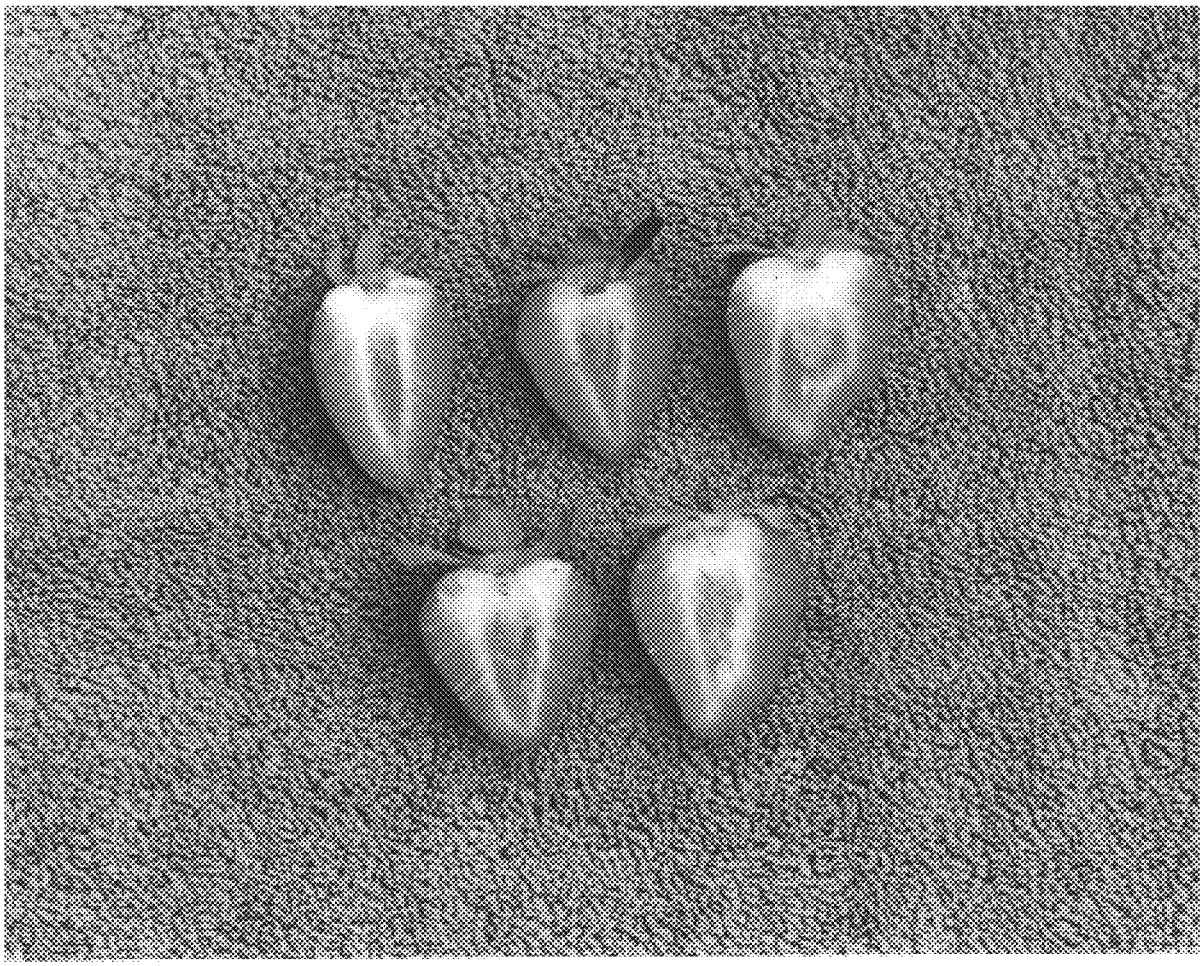
FIG. 5 shows the fruit in longitudinal cross-section.

The following detailed description of the new variety is based upon recorded observations of plants and fruit grown in Monterey County, Calif., U.S.A. Observations of 'Commander', 'San Juan' and 'Ana Maria' were taken side-by-side comparison in 2000. This description is in accordance with terminology used by the International Union for the Protection of New Varieties of Plants (UPOV). Color designations, color descriptions, and other phenotypical descriptions may deviate from the stated values and descriptions depending upon variation in environmental, seasonal, climatic and cultural conditions. Where colors are described herein, the most similar color designations are provided from The Royal Horticultural Society (R.H.S) Colour Chart.

PROPAGATION

The new variety is principally propagated by way of stolons. Although propagation by stolons is presently preferred, other known methods of propagating strawberry plants may be employed.

CHARACTERISTICS OF THE NEW VARIETY

Information on the new variety is presented in Tables 1, 2, 3 and 4. The flowers described in the tables are secondary flowers except where indicated. The fruit described is the secondary fruit on one-year-old plants. Fruit and flower measurements are an average of both primary and secondary fruit and flowers. Additional charateristic of the fruit of 'Sonora' include a medium acidity, having an average titratable acidity of 1.13%, an average brix of 11.8%, and the vascular tissue in 'Sonora' fruit is white (155D) in color. Characteristics of the stolons are also included in the Tables. In 2001, 'Sonora' produced an average of 33 daughter plants per mother plant in a low-elevation nursery, while 'San Juan' produced an average of 61 daughters/mother plant, indicating fewer stolons were produced by 'Sonora'. The time of first flowering of 'Sonora' in the Watsonville area is late February to early March.

Table 1 provides information on the plant and fruit characteristics of the new variety 'Sonora' compared with characteristics of the varieties 'Commander', 'San Juan' and 'Ana Maria'. Table 2 provides additional information of the plant and fruit characteristics of the new variety 'Sonora' compared with characteristics of the varieties 'Commander', 'San Juan' and 'Ana Maria'. Table 3 provides the new variety's reactions to stress, pests, and diseases as compared to the varieties 'Commander', 'San Juan' and 'Ana Maria'.

In addition to morphological descriptions, the new cultivar 'Sonora' has been analyzed to obtain an indication of its genetic makeup to provide further means for identifying the new variety and distinguishing it from other somewhat similar and/or related strawberry varieties. Specifically, leaf samples of 'Sonora', 'Commander', 'San Juan' and 'Ana Maria' were analyzed by electrophoresis for isozyme patterns of the enzymes phosphoglucoisomerase (PGI), leucine aminopeptidase (LAP) and phosphogluomutase (PGM). See e.g., J. Amer. Soc. Hort. Sci. 106:684–687. Table 4 provides isozyme characteristics of the new variety as compared to the varieties 'Commander', 'San Juan' and 'Ana Maria'.

TABLE 1

Detailed comparison of 'Sonora', 'Commander', 'San Juan' and 'Ana Maria'

| | 'Sonora' | 'Commander' | 'San Juan' | 'Ana Maria' |
|---|---|---|---|---|
| Plant Characteristics | | | | |
| Height of Plant (cm) | 25.3 | 24.6 | 24.3 | 30.6 |
| Spread of Plant (cm) | 43.9 | 47.1 | 43.2 | 50.0 |
| Number of Crowns | 6.0 | 4.7 | 5.7 | 5.6 |

TABLE 1-continued

Detailed comparison of 'Sonora', 'Commander', 'San Juan' and 'Ana Maria'

| | 'Sonora' | 'Commander' | 'San Juan' | 'Ana Maria' |
|---|---|---|---|---|
| Leaf Characteristics | | | | |
| Terminal Leaflet Length | 6.0 | 7.5 | 7.5 | 8.0 |
| Terminal Leaflet Width (cm) | 6.4 | 7.4 | 7.6 | 8.2 |
| Terminal Leaflet Length/Width Ratio | 0.92 | 1.02 | 0.99 | 0.98 |
| # Teeth/Terminal Leaflet | 20.6 | 16.9 | 20.1 | 19.7 |
| Color of upperside | 147A medium to dark green | 147A medium green | 147A dark green | 147A medium green |
| Color of underside | 148B light gray green | 148B light gray green | 148C light gray green | 148B light gray green |
| Petiole Length (cm) | 18.8 | 20.2 | 21.7 | 21.9 |
| Petiole Color | 145A | 145A | 145A | 145B |
| Bract Frequency | 0% | 20% Typically single | 60% Typically paired | 50% Typically paired |
| Stipule Length (cm) | 3.1 | 3.1 | 3.8 | 3.4 |
| Stipule Width (cm) | 0.9 | 0.9 | 0.8 | 0.7 |
| Flower Characteristics | | | | |
| Petal Length (cm) | 1.17 | 1.16 | 1.23 | 1.38 |
| Petal Width (cm) | 1.23 | 1.17 | 1.26 | 1.37 |
| Petal Length/Width Ratio | 0.95 | 0.99 | 0.98 | 1.01 |
| Flower Diameter (cm) | 2.99 | 2.94 | 3.05 | 3.40 |
| Calyx Diameter (cm) | 3.48 | 3.28 | 3.58 | 3.79 |
| Flower Color | 155C | 155C | 155D | 155C |
| Fruit Characteristics | | | | |
| Fruit Length (cm) | 4.7 | 4.6 | 4.8 | 4.6 |
| Fruit Width (cm) | 4.0 | 4.1 | 4.3 | 3.7 |
| Fruit Length/Width Ratio | 1.17 | 1.12 | 1.12 | 1.24 |
| Average Berry Weight (g) | 22.4 | 23.9 | 26.1 | 19.3 |
| External Color | 53A dark red | 45B orange red | 46A red | 46A red |
| Internal Color | 45A dark red | 44B orange red | 44A medium red | 44B orange red |
| Achene Coloration | 53A and 17A dark red and yellow | 46A and 14A dark red and yellow | 46A and 16A dark red and yellow | 46B and 16A dark red and yellow |
| Yield (g/plant) | 1367 | 1400 | 1212 | 1327 |

TABLE 2

Characterisitcs of 'Sonora', 'Commander', 'San Juan' and 'Ana Maria'

| | 'Sonora' | 'Commander' |
|---|---|---|
| Plant | | |
| Habit | flat globose | flat globose |
| Density | dense | medium |
| Vigor | medium | medium |
| Leaf | | |
| Shape in cross section | concave | flat |
| Interveinal blistering | strong | weak |
| Glossiness | weak | medium to strong |
| Number of leaflets | 3 only | 3 only |
| Terminal leaflet margin profile | flat | revolute to flat |
| Terminal leaflet shape of base | rounded | rounded |
| Terminal leaflet shape of | rounded | rounded |

TABLE 2-continued

| Characterisitcs of 'Sonora', 'Commander', 'San Juan' and 'Ana Maria' | | |
|---|---|---|
| teeth | | |
| Stipule pubescence | sparse | medium dense |
| Petiole pubescence | sparse | medium |
| Petiole pose of hairs | outward | outward |
| Stolon | | |
| Number | few to medium | medium to many |
| Anthocyanin coloration | medium | — |
| Thickness | medium | — |
| Pubescence | dense to very dense | — |
| Inflorescence | | |
| Position relative to foliage | above | level with to above |
| Diameter of calyx relative to corolla on secondary flowers | larger | same size to larger |
| Diameter of inner calyx relative to outer on secondary flowers | same size | same size |
| Spacing of petals | overlapping | overlapping |
| Fruiting Truss | | |
| Attitude at first picking | semi-erect | prostrate |
| Length (cm) | 30.3 | 33.0 |
| Fruit | | |
| Predominant shape | conical | conical to bi-conical |
| Difference in shapes between primary and secondary fruits | very slight to slight | slight |
| Band without achenes | very narrow to narrow | narrow to medium |
| Unevenness of surface | very weak | weak |
| Evenness of color | even | slightly uneven |
| Glossiness | weak to medium | strong |
| Insertion of achenes | below to level with surface | level with surface |
| Insertion of calyx | level to in a basin | level |
| Pose of the calyx segments | spreading to reflexed | spreading |
| Size of calyx in relation to fruit on secondary fruit | same size to larger | same size |
| Adherence of calyx | strong | strong |
| Firmness of flesh | medium | medium |
| Evenness of flesh color | even | slightly uneven |
| Distribution of flesh color | marginal and central | marginal and central |
| Hollow center size | absent to small | medium |
| Sweetness | medium to strong | medium to strong |
| Texture when tasted | medium | medium |
| Acidity | medium | medium to weak |
| Time of Flowering | medium | early to medium |
| Harvest Interval | Mid-April to Early November | Mid-April to Early November |
| Type of Bearing | fully everbearing | partially everbearing |

| | 'San Juan' | 'Ana Maria' |
|---|---|---|
| Plant | | |
| Habit | globose to flat globose | globose to upright |
| Density | medium | open |
| Vigor | medium | strong |
| Leaf | | |
| Shape in cross section | flat to slightly convex | concave |
| Interveinal blistering | medium to strong | medium to strong |
| Glossiness | weak to medium weak | medium |

TABLE 2-continued

| Characterisitcs of 'Sonora', 'Commander', 'San Juan' and 'Ana Maria' | | |
|---|---|---|
| Number of leaflets | sometimes more than 3 leaflets (approx. 17% of leaves) | 3 only |
| Terminal leaflet margin profile | revolute to flat | flat |
| Terminal leaflet shape of base | obtuse to rounded | rounded to slightly oblique |
| Terminal leaflet shape of teeth | rounded | obtuse |
| Stipule pubescence | medium dense | sparse |
| Petiole pubescence | medium | sparse |
| Petiole pose of hairs | outward to downward | outward |
| Stolon | | |
| Number | medium to many | medium to many |
| Anthocyanin coloration | strong | strong |
| Thickness | medium | medium |
| Pubescence | medium | medium to dense |
| Inflorescence | | |
| Position relative to foliage | beneath to level with | level with to above |
| Diameter of calyx relative to corolla on secondary flowers | larger | smaller to same size |
| Diameter of inner calyx relative to outer on secondary flowers | same size | smaller to same size |
| Spacing of petals | overlapping | overlapping |
| Fruiting Truss | | |
| Attitude at first picking | prostrate | semi-erect |
| Length (cm) | 28.5 | 33.3 |
| Fruit | | |
| Predominant shape | conical to almost cylindical | conical |
| Difference in shapes between primary and secondary fruits | moderate | none to very slight |
| Band without achenes | narrow | narrow to medium |
| Unevenness of surface | medium | very weak to weak |
| Evenness of color | even | even |
| Glossiness | very strong | strong |
| Insertion of achenes | level with surface | below to level with surface |
| Insertion of calyx | level | level to set above |
| Pose of the calyx segments | spreading to reflexed | spreading |
| Size of calyx in relation to fruit on secondary fruit | same size | same size to larger |
| Adherence of calyx | strong | weak to medium |
| Firmness of flesh | firm | firm |
| Evenness of flesh color | slightly uneven to even | slightly uneven |
| Distribution of flesh color | marginal and central | marginal and central |
| Hollow center size | medium | small |
| Sweetness | medium to strong | medium to strong |
| Texture when tasted | medium | medium |
| Acidity | medium | medium |
| Time of Flowering | medium to late | medium to late |
| Harvest Interval | Mid-April to Early November | Mid-April to Early November |
| Type of Bearing | partially everbearing | partially everbearing |

TABLE 3

Reactions to Stress, Pests, and Diseases for 'Sonora', 'Commander', 'San Juan' and 'Ana Maria'

| | 'Sonora' | 'Commander' | 'San Juan' | 'Ana Maria' |
|---|---|---|---|---|
| Reaction to Stress | | | | |
| high pH | moderately resistant | moderately resistant | moderately resistant | moderately resistant |
| high soil salt levels | moderately resistant | moderately resistant | moderately resistant | moderately resistant |
| Reaction to Pests | | | | |
| *Tetranychus urticae* | moderately susceptible | moderately susceptible | moderately susceptible | moderately susceptible |
| Aphis spp. | susceptible | suceptible | susceptible | susceptible |
| *Lygus hesperus* | susceptible | suceptible | susceptible | susceptible |
| Reaction To Diseases | | | | |
| Botrytis fruit rot | susceptible | susceptible | susceptible | susceptible |
| Powdery mildew | susceptible | moderately resistant | moderately resistant | moderately resistant |
| Verticillium wilt | moderately resistant | susceptible | susceptible | susceptible |
| Strawberry Mottle Virus | moderately resistant | moderately resistant | moderately resistant | moderately resistant |

TABLE 3-continued

Reactions to Stress, Pests, and Diseases for 'Sonora', 'Commander', 'San Juan' and 'Ana Maria'

| | 'Sonora' | 'Commander' | 'San Juan' | 'Ana Maria' |
|---|---|---|---|---|
| *Xanthomonas fragariae* | moderately resistant | moderately resistant | moderately resistant | moderately resistant |

TABLE 4

Isozyme Analysis for 'Sonora', 'Commander', 'San Juan' and 'Ana Maria'

| Locus | 'Sonora' | 'Commander' | 'San Juan' | 'Ana Maria' |
|---|---|---|---|---|
| PGI | A2 | A4 | A2 | A1 |
| LAP | B3 | B3 | B3 | B3 |
| PGM | C4 | C4 | C4 | C4 |

What is claimed is:

1. A new and distinct variety of strawberry plant, substantially as shown and described.

* * * * *